United States Patent [19]
Dümpelmann et al.

[11] Patent Number: 5,852,211
[45] Date of Patent: Dec. 22, 1998

[54] PROCESS FOR THE CONVERSION OF THE SODIUM SALT OF 2-KETO-L-GULONIC ACID TO THE FREE ACID

[75] Inventors: Ralf Dümpelmann, Sisseln, Switzerland; Tomislav Keglevic, Gumpoldskirchen, Austria

[73] Assignee: Roche Vitamins Inc., Parsippany, N.J.

[21] Appl. No.: 842,923

[22] Filed: Apr. 17, 1997

[30]    Foreign Application Priority Data

Apr. 30, 1996 [EP] European Pat. Off. .............. 96106829
Feb. 20, 1997 [EP] European Pat. Off. .............. 97102766

[51] Int. Cl.$^6$ .................................................. C07C 51/42
[52] U.S. Cl. ........................................... 562/580; 562/587
[58] Field of Search ..................... 562/580, 587

[56]    References Cited

U.S. PATENT DOCUMENTS

| | | |
|---|---|---|
| 3,381,027 | 4/1968 | Jaffe et al. . |
| 4,491,668 | 1/1985 | Ikawa et al. ............................ 549/315 |
| 4,990,441 | 2/1991 | Barthole et al. . |
| 5,128,487 | 7/1992 | Tomislav et al. . |
| 5,391,770 | 2/1995 | Le Fur et al. . |

FOREIGN PATENT DOCUMENTS

| | | |
|---|---|---|
| 1122802A | 5/1996 | China . |
| 091 134 | 10/1983 | European Pat. Off. . |
| 359 042 | 3/1990 | European Pat. Off. . |
| 359 645 | 3/1990 | European Pat. Off. . |
| 403 993 | 12/1990 | European Pat. Off. . |

OTHER PUBLICATIONS

Derwent Abstract No. 97–490828 of Chinese Patent Publication No. 1122802A, 1996.
Derwent Abstract No. AN–90–084893/12.
*Chemical Abstracts*, 124(5):#56570 (1996).
*Helv. Chim. Acta.*, 17:311–328 (1934) (no translation).
*Comprehensive Analytical Chemistry*, 16:355–392 (1982).
Derwent Abstract No. AN–1979:136274—JP 53 062 894.
Derwent Abstract No. AN–1977:582601—JP 52 066 684.

*Primary Examiner*—Samuel Barts
*Attorney, Agent, or Firm*—George W. Johnston; Dennis P. Tramaloni; Bruce A. Pokras

[57]    ABSTRACT

A process for the conversion of the sodium salt of 2-keto-L-gulonic acid, which is present in an aqueous fermentation solution, into an alcoholic solution of the free acid and, if desired, into an alkyl ester of the acid comprises a) recovering the sodium 2-keto-L-gulonate monohydrate from an aqueous fermentation solution by crystallization involving evaporation, cooling or displacement and, if desired, pulverizing the thus-obtained crystallizate by grinding, b1) suspending the optionally ground sodium 2-keto-L-gulonate monohydrate obtained in step a) in a lower alcohol, leaving the crystals to swell and thereafter adding an acid of low water content, whereby the measured pH value should lie above 1.5, or b2) adding the optionally ground sodium 2-keto-L-gulonate monohydrate obtained in step a) together with an about stoichiometric amount of an acid of low water content to a lower alcohol using a wet grinding system, whereby the measured pH value should lie above 1.5, or b3) carrying out a combination of steps b1) and b2) including recycling of product streams, and c) separating the salt of the added acid formed in step b1), b2) or b3) and thus obtaining an alcoholic solution of 2-keto-L-gulonic acid, and, if desired, d) treating the alcoholic solution of 2-keto-L-gulonic acid obtained in step c) with a catalytic amount of an acid or with an acidic cation exchanger in order to esterify the 2-keto-L-gulonic acid with the alcohol to give the corresponding lower alkyl 2-keto-L-gulonate.

18 Claims, No Drawings

PROCESS FOR THE CONVERSION OF THE SODIUM SALT OF 2-KETO-L-GULONIC ACID TO THE FREE ACID

BACKGROUND OF THE INVENTION

The present invention is concerned with a novel process for the conversion of a sodium salt of 2-keto-L-gulonic acid dissolved in an aqueous fermentation solution into an alcoholic solution of the free acid by crystallization of the salt as the monohydrate from the fermentation solution and subsequent protonation to 2-keto-L-gulonic acid by reaction of the salt with a strong acid in alcoholic medium.

As is known, 2-keto-L-gulonic acid (KGA) is an important starting material for the manufacture of ascorbic acid (vitamin C). In fermentative processes for the manufacture of KGA, the KGA which results as a metabolic product is neutralized by the addition of a base, e.g. sodium hydroxide or calcium hydroxide, in order to maintain favorable fermentation conditions. The product of the fermentation is an aqueous, biomass-containing fermentation solution in which the KGA salt, i.e. the sodium or calcium 2-keto-L-gulonate [NaKGA or Ca(KGA)$_2$, respectively], is present in dissolved form.

For the industrial manufacture of ascorbic acid or of the ascorbate, the fermentatively produced KGA must be transferred into an organic solvent. A lower alkanol is advantageously used as the solvent. The ascorbate is obtained in high yield by esterifying the alcohol with KGA and subsequently adding a base. As an alternative to this, the KGA can be converted into ascorbic acid in an organic solvent under strongly acidic conditions. However, the yields are as a rule somewhat lower [see Helv. Chim. Acta 17, 311–328 (1934)].

All processes for the working up of the fermentation solution are based on three process steps:

1. Protonation of the sodium or calcium 2-keto-L-gulonate present to the free acid (e.g. NaKGA+H$^+$→KGA+Na$^+$);
2. Removal of water;
3. Removal of the biomass, dissolved proteins and other contaminants present in the fermentation solution.

The sequence in which the process steps are carried out and their specific performance are characteristic of the respective process.

The protonation (Step 1) can be effected in the aqueous fermentation solution by the addition of acids. According to U.S. Pat. No. 3,381,027 and European Patent Publication (EP) 359 645 the dissolved KGA is obtained by adding sulphuric acid to Ca(KGA)$_2$ and separating the precipitated calcium salt. A protonation can also be effected by using cation exchange resins. According to EP 359 645 the aqueous Ca(KGA)$_2$-containing fermentation solution is passed through a cation exchanger and the calcium ions are removed completely. When cation exchangers are used, the biomass must previously be removed completely (Step 3), e.g. by microfiltration, in order to guarantee a sufficiently long useful life of the cation exchanger.

The product of the protonation is an aqueous, KGA-containing solution having a pH value which is significantly below 2.0 (the pK$_s$ value of KGA is 2.54). KGA is thereupon isolated by crystallization, extraction (e.g. according to EP 359 042) or adsorption (e.g. according to Chinese Patent Publication 1097731A: see Chem. Abs. 124, 56570) and thereby separated from the water (Step 2). The crystallization of KGA in high yields can only be effected with difficulty, since the solubility, e.g. 480 g/l at 30° C., is very high. Extraction and adsorption are industrially difficult processes, especially when contaminants from the fermentation are present. According to EP 359 042 the biomass must accordingly be removed completely prior to the extraction.

According to EP 403 993 isolated, but not purified KGA can be used for the manufacture of sodium ascorbate. Contaminants, such as biomass and proteins, are eliminated in further process operations by the addition of sodium bicarbonate or potassium bicarbonate and precipitation of non-esterified KGA.

In all previously known processes the protonation of KGA is effected first and then the water is removed. In principle, however, it is possible to operate in reverse, i.e. to firstly isolate the NaKGA or Ca(KGA)$_2$ from the fermentation solution, thereby to remove water (Step 2), and subsequently to carry out the protonation (Step 1). Thus, the crystallization of sodium 2-keto-L-gulonate monohydrate (NaKGA.H$_2$O) is known from Japanese Patent Publications (Kokai) 66684/1977 and 62894/1978, and in the case of solubilities of e.g. 250 g/l at 30° C. significantly higher yields are to be expected than in the crystallization of KGA.H$_2$O. Moreover, both substances crystallize as the monohydrate, which usually is not taken into consideration. The difficulty in this operational mode, i.e. Step 2 prior to Step 1, lies in the complete protonation of the NaKGA in organic solvents, since NaKGA is practically insoluble.

Some attempts to protonate NaKGA in organic solvents have, however, been documented.

According to EP 91 134 crystalline NaKGA can be converted into KGA using gaseous hydrogen chloride in a mixture of ethanol and acetone. The sodium chloride, which is also formed, is separated. In the further course of the reaction a rearrangement to crystalline ascorbic acid takes place immediately under the strong acidic reaction conditions, with undesired byproducts resulting and the yields therefore being low at 60–82%.

According to U.S. Pat. No. 5,391,770 NaKGA can be reacted with a more than 40% excess of concentrated sulphuric acid in methanol (Example 10). The reaction time inclusive of esterification to the methyl ester amounts to 4.5 hours at 65° C. and the yield is 91.9%. Subsequently, the pH is increased to 4 and the sodium sulphate is separated. Having regard to these long reaction times and the large excess of acid, considerable amounts of decomposition products are to be expected according to EP 403 993.

EP 403 993 discloses the reaction of a mixture of 50% KGA and 50% NaKGA with an about 50% excess of sulphuric acid in methanol (Example 5). After a reaction period of one hour under reflux conditions the mixture is filtered. The yield of sodium sulphate obtained corresponds to about 60% of theory. Accordingly, a maximum of 50% of the KGA can be used in the form of the sodium salt. Fundamentally, the process provides for the use of KGA, with the mentioned NaKGA resulting and being recycled in subsequent steps.

Disadvantages in the last two processes are the large excess of sulphuric acid used and the long reaction times under strong acidic conditions. When sulphuric acid is added in stoichiometric amounts and thus under milder conditions, a considerable part of the NaKGA usually remains incorporated in the sodium sulphate which results and the yield drops accordingly.

According to U.S. Pat. No. 5,391,770 it is also known that the sodium salt of ascorbic acid (NaASC) can be protonated to ascorbic acid by the addition of sulphuric acid in methanol. In this case NaKGA is present as an impurity in up to 9%. In methanol as the solvent the yields of ascorbic acid are between 91% and 96% (Examples 12, 14 and 15). On the other hand, in a solvent mixture of 75% methanol and 25% water the yield of ascorbic acid is 99% (Example 2). Clearly, the yields in pure solvent are considerably lower than in the solvent mixture, since a preferred water content of 15–25% is indicated. The reason is the higher solubility of NaASC in the mixture compared with the pure solvent, e.g. at 40° C. about 2 weight percent (wt. %) compared with about 0.3 wt. %.

Material transport is impeded in the case of low solubilities and the reaction of a difficultly soluble salt with sulphuric acid to give the very difficultly soluble sodium sulphate (solubility=0.024 wt. % in methanol) gives correspondingly poorer yields. Material transfer problems are to be expected to an increasing extent in the case of a reaction involving $NaKGA.H_2O$, since the solubilities are considerably lower than those of sodium ascorbate (at 40° C., <0.01 wt. % in methanol, <0.1 wt. % in 90% methanol/10% water).

SUMMARY OF THE INVENTION

The object of the present invention is to provide a process which permits in the simplest possible manner the conversion of the sodium salt of 2-keto-L-gulonic acid, which is present in an aqueous, non-purified fermentation broth, into free 2-keto-L-gulonic acid in alcoholic solution in high yield and with high purity. At the same time, the disadvantages of prior art processes, especially the complete removal of biomass, proteins, etc., e.g., by microfiltration, the use of cation exchangers to remove metal ions from the aqueous fermentation solutions as well as the crystallization or drying of 2-keto-L-gulonic acid, should be avoided. Moreover, only readily accessible chemicals should be used, and as few steps as possible should be required.

In the scope of the present invention a process has now been found which fulfills the aforementioned requirements and in accordance with which the sodium salt of 2-keto-L-gulonic acid is crystallized from a fermentation solution, which is only partially freed from biomass, and the sodium 2-keto-L-gulonate monohydrate obtained is converted into an alcoholic solution of free 2-keto-L-gulonic acid. The protonation to 2-keto-L-gulonic acid and the removal of the metal ions are effected in this case exclusively by reaction in an alcoholic medium. Particular reaction conditions have now been found under which sodium 2-keto-L-gulonate monohydrate ($NaKGA.H_2O$) suspended in alcoholic medium reacts in very good yields with an acid of low water content to give the dissolved, free 2-keto-L-gulonic acid (KGA) and an insoluble salt. For the first time by this means the crystallization of the $NaKGA.H_2O$ from the aqueous fermentation solution is practicable. The critical steps required in the previous methods, such as the passage of the fermentation solution over a cation exchanger and crystallization or drying of KGA, are thereby avoided.

As a result of the process in accordance with the invention, the KGA is present in alcoholic solution and can then be esterified directly in high yields in any manner and converted into ascorbate. Accordingly, a sequence of process steps is characteristic of the process in accordance with the invention, i.e., firstly $NaKGA.H_2O$ is crystallized from a fermentation broth, i.e., the water other than the water of crystallization is removed completely (Step 2, see above), and thereafter the protonation (Step 1) is effected entirely in a lower alkanol as the solvent by the addition of a strong acid (of low water content), e.g., sulphuric acid. A difficultly soluble salt of the acid, e.g., sodium sulphate, results and can be separated readily. The desired solution of KGA remains and, as mentioned above, can be esterified directly and converted into ascorbate. Also characteristic are special reaction conditions for the protonation in which, in spite of extremely low solubilities of the $NaKGA.H_2O$ used and of the product, e.g., sodium sulphate, yields of more than 97% can be realized. In this respect, specific and previously unknown properties pertaining to $NaKGA.H_2O$ as a material are made use of, as will be explained in more detail below.

DETAILED DESCRIPTION OF THE INVENTION

The present invention is a process for the conversion of the sodium salt of 2-keto-L-gulonic acid from aqueous fermentation solutions into an alcoholic solution of the free acid, which process comprises:

a) crystallizing sodium 2-keto-L-gulonate monohydrate from an aqueous fermentation solution;

b) separating the sodium 2-keto-L-gulonate monohydrate crystals from the aqueous fermentation solution;

c) suspending the sodium 2-keto-L-gulonate monohydrate in a lower alcohol with acid at a pH in a range from about 1.5 to about 3.5 whereby the acid is converted to the insoluble sodium salt of the acid and the sodium 2-keto-L-gulonate monohydrate is converted to free 2-keto-L-gulonic acid;

d) removing the sodium salt of the acid to obtain an alcoholic solution of 2-keto-L-gulonic acid.

The free 2-keto-L-gulonic acid may thereafter be esterified by the alcohol of the alcoholic solution obtained in step d) to afford the appropriate alkyl ester of the acid. If this is to be done, the acid used to form the sodium salt is preferably a concentrated acid to limit the amount of water which is added to the reaction mixture.

The crystallization may be carried out by any conventional means. Preferably, the crystallization is carried out by evaporation, cooling or displacement. In a preferred embodiment of the invention, the crystals of the $NaKGA.H_2O$ are ground prior to being suspended in the lower alkanol with the acid. Regardless of whether the crystals are ground or not, it is preferred that the $NaKGA.H_2O$ crystals are permitted to swell after being suspended in the lower alkanol prior to the addition of the acid.

Thus a preferred embodiment of the process of the invention comprises:

a) recovering the $NaKGA.H_2O$ from an aqueous fermentation solution by crystallization, involving evaporation, cooling or displacement and, if desired, pulverizing the thus-obtained crystallizate by grinding, b1) suspending the optionally ground $NaKGA.H_2O$ obtained in step a) in a lower alcohol, leaving the crystals to swell and thereafter adding an acid of low water content, whereby the measured pH value should lie above 1.5, or b2) adding the optionally ground $NaKGA.H_2O$ obtained in step a) together with an about stoichiometric amount of an acid of low water content to a lower alcohol using a wet grinding system, whereby the measured pH value should lie above 1.5, or b3) carrying out a combination of steps b1) and b2) including recycling of product streams, and c) removing the salt of the added acid formed in step b1), b2) or b3) and thus obtaining an alcoholic solution of KGA, and, if desired, d) treating the alcoholic solution of KGA obtained in step c) with a catalytic amount of an acid or with an acidic cation exchanger in order to esterify the KGA with the alcohol.

The fermentation, which is effected prior to the actual process in accordance with the invention by any conventional means, yields a turbid fermentation broth containing biomass. The crystallization of the NaKGA present in the fermentation broth to the NaKGA.H$_2$O can in principle be effected directly from this broth; however, a previous separation of at least 90% of the biomass by centrifugation has been shown to be advantageous, and is therefore preferred. A turbid, but sludge-free fermentation solution results in this case. A complete removal of biomass and dissolved proteins prior to the crystallization is, however, not necessary.

The crystallization of the NaKGA.H$_2$O from the aqueous fermentation broth or solution may be effected in a manner known per se, e.g., by concentrating the fermentation broth or solution, cooling the solution or adding a different solvent, i.e., by evaporation, cooling or displacement crystallization, respectively. The conventional conditions for carrying out the chosen method of crystallization may be used. Thus, for example, evaporation crystallization is preferably carried out under reduced pressure and at the same time at a low temperature, preferably at temperatures in the range of about 35° C. to about 60° C., in order to avoid as far as possible decomposition of the product. The crystallization can be carried out continuously or batch-wise, preferably continuously. Continuous evaporation crystallization is the crystallization method which is preferably used. Subsequently, the crystallizate can be separated from the fermentation mother liquor by any conventional solid/liquid separating operation, such as filtration or centrifugation. The NaKGA.H$_2$O crystallizate obtained is, under the given conditions, usually purer than 98% with small amounts of organic contaminants (<500 ppm nitrogen). Such small amounts of organic contaminants can, however, be eliminated subsequently in an advantageous manner.

In the next process step the crystallizate in crystalline form or optionally in a form reduced in size by grinding is firstly suspended in a lower alkanol, e.g., methanol, ethanol, propanol or 1,2-ethanediol (glycol), preferably methanol.

It has now been found that the NaKGA.H$_2$O converts into the anhydrate (NaKGA) on losing the water in the alcohol and thereby forms a large number of very thin needles (<2 mm). These needles have a substantially larger surface than the monohydrate used, as a result of which surface-dependent reactions are favored. This mode of dehydration with the formation of new, needle-shaped crystals has hitherto only been observed by temperature increase [see in this respect "Dehydration of Methandriol" in M. Kuhnert-Brandstätter, Theromicroscopy of Organic Compounds, Wilsons and Wilson's Comprehensive Analytical Chemistry, G. Svehla (Ed.), Elsevier, Amsterdam, Vol. 16, p. 355 (1982)]. Thus, it is theorized that the following reactions occur during the process of the invention on the basis of this specific property of the NaKGA.H$_2$O:

1. Dehydration (upon addition to the alcohol)
   2 NaKGA.H$_2$O (undissolved)→2NaKGA (undissolved, needles)+2H$_2$O
2. Protonation (e.g., using H$_2$SO$_4$ as the acid)
   2 NaKGA (undissolved, needles)+H$_2$SO$_4$→2KGA (dissolved)+Na$_2$SO$_4$ (undissolved)

A strong acid of low water content is used for the protonation. The water content of the added acid is not critical for the process. However, the concentration of water in the resulting 2-keto-L-gulonic acid/alcohol solution determines the equilibrium conversion of a subsequent esterification. Therefore, from an industrial-economical point of view, acids of low water content, i.e., acids which are more appropriately denoted as "concentrated", are therefore preferably used. As acids of low water content there conveniently come into consideration concentrated mineral acids such as, for example, (in each case concentrated) sulphuric acid, nitric acid, hydrochloric acid and phosphoric acid, and even gaseous hydrogen chloride. Concentrated sulphuric acid or hydrochloric acid is particularly preferred. Especially preferred is >95% sulphuric acid, because its sodium salt, sodium sulphate, is practically insoluble in an alcoholic medium and can accordingly can be separated readily from the reaction mixture. The acid is preferably added in stoichiometric amounts or in a slight excess (in general a less than 5 per cent excess).

As a consequence of the suspension of the sodium salt in the lower alcohol the crystals of the salt swell.

Reaction conditions which facilitate reactions 1. and 2. are characteristic of the process in accordance with the invention. The following applies with respect to three possible means of carrying out the process of the invention (process variants b1), b2) and b3) hereinabove):

High yields are achieved when the NaKGA.H$_2$O crystals are firstly suspended in the alcoholic solvent and thereby swell (conversion of the NaKGA.H$_2$O via dehydration into needle-shaped crystal forms of NaKGA having a large surface). In this case the needles form within seconds to hours depending on the particle size of the material used and on the intensity of stirring. Preferably, either fine material (<100 μm) or/and an intensive stirrer or disperser is used. The needles then normally form in significantly less than 10 minutes. Preferably, less than 10 wt. % NaKGA.H$_2$O based on the solvent (lower alcohol) is used, since the suspension is very difficult to stir because of the needle formation. Higher concentrations can be realized by repeating reactions 1. and 2. or other recyclizations. At the conclusion of the needle formation the acid is introduced, whereby the resulting pH value should lie in a range from about 1.5 to about 3.5, preferably between 2.5 and 3.5. At lower pH values more NaKGA is incorporated into the salt of the added acid and increasing amounts of undesired byproducts are formed, especially with sulphuric acid.

High yields can also be achieved when the NaKGA.H$_2$O and the acid are added simultaneously, but the particles have preferably been reduced in size by wet milling, such as, e.g., using rotor-stator dispersion machines, homogenizers, ultrasonic or similar devices. Here the pH value of the resulting mixture should also be in a range from about 1.5 to about 3.5, preferably 2.5–3.5, in order that the reaction does not proceed too rapidly and needle formation, which facilitates the reaction, takes place at least to a microscopic extent. The reaction time is usually less than 20 minutes; longer times are required after wet grinding. The average particle size of the resulting salt of the added acid should be a maximum of 10 μm, preferably <3 μm.

The high energy input required for the wet grinding is a disadvantage. However, the simple reaction procedure, especially the avoidance of a difficultly stirrable suspension, is an advantage.

Combinations of the procedures described immediately above are advantageously used. For example, either the needle formation or the addition of acid can be effected in successive reactors and the wet grinding can be performed in a further one. Further, in a continuous process the needle formation of unground NaKGA.H$_2$O can be effected in a first step and a wet grinding with addition of the acid can be effected in the subsequent step. Moreover, the difficultly soluble salt of the added acid can be selectively recycled, for example, by means of a hydrocyclone. By this means the residence times of the difficultly soluble salt of the added acid are increased and the achievable yields are once again increased. A sodium sulphate, which contains considerable amounts of NaKGA.H$_2$O, can also be suspended in the solvent. The typical needles form and the reaction with the acid can be realized with high yields without grinding the crystals.

The temperature at which the dehydration and acid reactions are carried out is not critical. Preferably, however, the temperatures lie in the range of about 20° C. to about 70° C. KGA is less soluble at lower temperatures, while decompositions occur at higher temperatures. In general, the reaction conditions are chosen such that practically no esterification reactions can take place. Significantly less than 5% ester usually results at the pH values >1.5 given herein. An esterification of the 2-keto-L-gulonic acid, which may be desired, can be effected without problems in a known manner in the presence of an acid as the catalyst after the removal of the insoluble salt of the added acid, e.g., of the sodium sulphate.

The pH values given herein relate to measurements using a pH glass electrode with 3 molar potassium chloride solution as the electrolyte. When other measuring instruments are used under otherwise identical conditions, pH values different therefrom can be measured.

The liberated 2-keto-L-gulonic acid should be soluble in the reaction medium under the chosen reaction conditions.

The separation of the difficultly soluble salt of the added acid as well as the optional esterification of the 2-keto-L-gulonic acid can in each case be carried out in a known manner. Thus, the separation of the salt can be carried out by conventional means, such as filtration and/or centrifugation, preferably by centrifugation. However, fundamentally all solid/liquid separation methods are conceivable for particles <10 μm. The clear solution of KGA obtained can subsequently be converted by conventional means into the corresponding ester by, e.g., the addition of a catalytic amount of an acid or by using an acidic ion exchanger, such as disclosed in EP 671 405.

If the above-described esterification is desired, the conversion of the NaKGA.H$_2$O to the free KGA is preferably carried out using anhydrous solvents and concentrated acids (of low water content), since water displaces the equilibrium of the subsequent esterification in an unfavorable manner. Of course, some water is often present, be it from concentrated 37% hydrochloric acid or recycled substance stream. However, for the most favorable esterification conditions, the water content should preferably not exceed 10%.

With the aid of the process in accordance with the invention 2-keto-L-gulonic acid, which is very important for the manufacture of vitamin C and which occurs as a dissolved salt in the aqueous fermentation solution, can be converted in a relatively simple and economical manner into the alcoholic solution of the free acid. The thus-obtained solution of 2-keto-L-gulonic acid has a very high purity and can be converted into ascorbic acid in a known manner.

A fundamental advantage of the process in accordance with the invention is that a turbid fermentation solution which still contains biomass can be used for the crystallization of the NaKGA.H$_2$O in high yield, i.e., significantly higher than 90%. By the subsequent reaction with an acid of low water content (protonation), there is formed a difficultly soluble salt with which residues of biomass or proteins can be separated to a large extent. Thus, a clear solution of KGA in the lower alcohol, which contains practically no biomass, can be obtained in high yield. The difficulty of a complete biomass or protein separation in the aqueous phase is thereby avoided.

The following Examples for the conversion of the sodium salt of 2-keto-L-gulonic acid from aqueous fermentation solutions into the alcoholic solution of the free acid show advantageous embodiments of the process in accordance with the invention, but they are not in any way intended to represent a limitation. All temperatures are given in degrees Celsius (°C.).

EXAMPLE 1

The sodium salt of 2-keto-L-gulonic acid (as the monohydrate; hereinafter NaKGA.H$_2$O) was crystallized from the fermentation broth as follows:

2195 g of an aqueous, biomass-containing fermentation broth were centrifuged for 10 minutes at 12000 g, which gave 2160 g of a turbid supernatant and 35 g of sludge, corresponding to 1.5%. The supernatant was concentrated under reduced pressure at 20° and the first crystallizate which separated was filtered off and washed with water. The wash water was combined with the residual solution. This was again concentrated at 20° and the second crystallizate was filtered off and washed with water. Recycling of the wash water, concentration, filtration and washing were carried out in the same manner for the third and fourth crystallizates.

Crystallization of 2160 g of centrifuged, turbid fermentation broth gave 132.90 g: 1st crystallizate with 99.3% purity (54% yield)

60.17 g: 2nd crystallizate with >99.5% purity (78.9% overall yield)

29.70 g: 3rd crystallizate with 96.6% purity (90.6% overall yield)

15.00 g: 4th crystallizate with 79.5% purity (95.5% overall yield)

The overall yield of the first three crystallizations was 91% with an average purity of about 99%

EXAMPLE 2

A centrifuged, but turbid, pre-concentrated fermentation broth was crystallized continuously in a 6 l crystallizer under a vacuum at 55°. In the stationary state 1550 g/h of fermentation solution were added continuously with 17.0 wt. % sodium 2-keto-L-gulonate (NaKGA), corresponding to 1.22 mol. On average 241 g/h of dry crystallizate with a NaKGA.H$_2$O content of 99% (1.02 mol/h) separated. There were also obtained 180 g/h of mother liquor containing 11.9% NaKGA (1.02 mol/h). A total of a further 0.08 mol/h of NaKGA was recovered in the rinsing and purification solutions. The nitrogen content of the mother liquor was >1 wt. %. The crystals contained 180 ppm nitrogen.

EXAMPLE 3

40.0 g of NaKGA.H$_2$O with a content of 99% (169 mmol) were suspended in 400 g of methanol at room temperature while stirring. A thick suspension, which was difficult to stir, resulted. After 20 minutes 8.73 g of 95% sulphuric acid (85 mmol) were added thereto within 5 minutes at a minimal pH of 2.0. After 10 minutes a further 20.0 g (85 mmol) of NaKGA.H$_2$O were added, 5 minutes later 4.4 g (42 mmol) of the 95% sulphuric acid (42 mmol) were added and the mixture was stirred for a further 10 minutes. The addition of 20 g of NaKGA.H$_2$O and 4.4 g of the 95% sulphuric acid was repeated one more time. After stirring at room temperature for 75 minutes the solution was filtered. 25.21 g of sodium sulphate with a 3.6% content of 2-keto-L-gulonic acid (KGA; 5 mmol) separated. The filtrate obtained contained 329 mmol of KGA and 3 mmol of methyl 2-keto-L- gulonate (MeKGA), which corresponded to a yield of 98%. Together with the KGA found in the filter residue the recovery was almost 100%.

EXAMPLE 4

80.0 g of NaKGA.H$_2$O with a content of 99.0% (338 mmol) and 17.63 g of 95% sulphuric acid (180 mmol) were dosed into 390 g of methanol within 15 minutes at 20°–35° and at a pH value greater than 2.5. A disperser having a rotor-stator system was operated in the reaction vessel for wet grinding. After dispersion for 60 minutes the suspension was filtered and the filter residue was washed with a small amount of methanol. The pH value remained constant at 2.5 during the dosing by the controlled addition of the sulphuric acid. A pH value of 2.6 was measured after 75 minutes. The filtrate obtained contained 330 mmol of KGA, corresponding to a yield of 98%. There were obtained 25.45 g of filter residue (sodium sulphate) with a KGA content of 5.7%, corresponding to 7 mmol. The determinable content of MeKGA was 0.04% in the filtrate (1 mmol) and was not detectable in the filter residue. The recovery of KGA and MeKGA in the filtrate together with the KGA found in the filter residue was accordingly almost 100%.

EXAMPLE 5

75.0 g of NaKGA.H$_2$O with a content of 99% (317 mmol) and 16.38 g of 95% sulphuric acid (159 mmol) were dosed into 375 g of methanol within 6 minutes at 60° and at a pH value of 2.5. A disperser with a rotor-stator system was operated in the reaction vessel for the wet grinding. After the addition the mixture was dispersed for a further 10 minutes, subsequently filtered and the filter residue was washed with about 10 ml of methanol and dried under reduced pressure. The filtrate obtained contained 303 mmol of KGA and 5 mmol of MeKGA, corresponding to a yield of 97%. There were obtained 24.14 g of filter residue (sodium sulphate) with a KGA content of 6.2%, corresponding to 8 mmol. The determinable content of MeKGA was 0.27% in the filtrate (0.5 mmol) and 0.04% in the filter residue. The recovery of KGA and MeKGA in the filtrate together with the KGA and the MeKGa found in the filter residue was accordingly almost 100%.

EXAMPLE 6

80.0 g of crystalline NaKGA.H$_2$O (338 mmol), obtained according to the procedure described in Example 2, and 14.00 g of 96% sulphuric acid (137 mmol) were dosed into 400 g of methanol within 4 minutes at 65° and at a pH value greater than 2.5. A further 4.14 g (41 mmol) of sulphuric acid, in total a 5% stoichiometric excess, were added during 2 minutes, during which the pH value fell to 2.0. A disperser with a rotor-stator system was operated in the reaction vessel for wet grinding. After 10 minutes the mixture was filtered and the filter residue was washed with 40 ml of methanol. The filtrate contained 314 mmol of KGA and 12.1 mmol of MeKGA. There were obtained 25.02 g of dried filter residue (sodium sulphate) containing 7.5 mmol of KGA and 0.5 mmol of MeKGA. The yield was 96.4% with a recovery of 98.8%.

EXAMPLE 7

80.0 g of crystalline NaKGA.H$_2$O (338 mmol), obtained according to the procedure described in Example 2, and 15.40 g of 96% sulphuric acid (151 mmol) were dosed into 400 g of 1,2-ethanediol within 4 minutes at 65° and at a pH greater than 2.5. A further 1.88 g of the sulphuric acid (41 mmol) were added within one minute, during which the pH value fell to 2.3. A disperser with a rotor-stator system was operated in the reaction vessel for wet grinding. After 10 minutes the mixture was filtered and the filter residue was washed with a small amount of 1,2-ethanediol. There were obtained 19.84 g of dried filter residue (sodium sulphate) containing 2.3 wt. % of KGA, corresponding to 2.4 mmol of KGA. The filtrate could not be analyzed satisfactorily because of the high boiling point of the solvent.

EXAMPLE 8

80.0 g of crystalline NaKGA.H$_2$O (338 mmol), obtained according to the procedure described in Example 2, and 9.92 g of 96% sulphuric acid (97 mmol) were dosed into 432 g of methanol having a 8% water content within 5 minutes at 65° and at a pH value of 2.5. A further 7.36 g of the sulphuric acid (72 mmol) were added within 3 minutes, with the pH value being a minimum 1.9 and 2.3 towards the end. A disperser with a rotor-stator system was operated in the reaction vessel for wet grinding. After 10 minutes the suspension was filtered and the filter residue was washed with 20 ml of methanol. There were obtained 23.43 g of dry filter residue containing 5.7% of KGA (6.9 mmol) and 0.2% of MeKGA (0.2 mmol). The filtrate contained 325 mmol of KGA and 3.5 mmol of MeKGA.

EXAMPLE 9

10.0 g of sodium sulphate, which contained a total of 17.0 mmol of NaKGA.H$_2$O, NaKGA and KGA, corresponding to 39.7% of KGA, were suspended in 100 ml of methanol at 20° C. A thick suspension formed after 20 minutes. 0.82 g of 95% sulphuric acid (79 mmol) was added slowly in such a manner that the pH value was always above 2.0. After stirring for one hour the pH value was 2.3. The suspension was filtered and the filter residue was washed with a small amount of methanol. This gave 7.0 g of filter residue (sodium sulphate) containing 0.12% of KGA. Evaporation of the filtrate under a vacuum gave 3.47 g of product containing 81.4% of KGA and 6.5% of MeKGA.

EXAMPLE 10

In each of ten successive experiments 400 g of methanol were placed in a 1 l reaction vessel and sodium sulphate from the respective preceding experiment was suspended therein. In each case 80.0 g of crystalline NaKGA.H$_2$O (3.38 mmol), obtained according to the procedure described in Example 2, were added over 5 minutes at 60° C. and in each case 17.5 g of 95% sulphuric acid (169 mmol) were added within 10 minutes at a pH value of about 2.5. A disperser with a rotor-stator system was operated in the reaction vessel for wet grinding. After a reaction period of a further 5 minutes the mixture was filtered and the moist filter residue (sodium sulphate) was used in the subsequent experiment. In the last experiment the filter residue was washed with 400 ml of methanol and dried. From the last experiment there were obtained 240 g of a dried filter residue (sodium sulphate) containing 3.9% of KGA and 0.3% of MeKGA (0.05 mol). The filtrate and wash water, total 3570 g, contained 16.6% of KGA (3.06 mol), 1.49% of MeKGA (0.25 mol) and 11 ppm nitrogen. 350 ppm nitrogen were determined in the sodium sulphate. The average particle size of the sodium sulphate fell over the series of experiments from 10 μm (1st experiment) to 3.7 μm (10th experiment).

We claim:

1. A process for the conversion of the sodium salt of 2-keto-L-gulonic acid from aqueous fermentation solutions into an alcoholic solution of the free acid comprising:

a) crystallizing sodium 2-keto-L-gulonate monohydrate from an aqueous fermentation solution;

b) separating the sodium 2-keto-L-gulonate monohydrate crystals from the aqueous fermentation solution;

c) suspending the sodium 2-keto-L-gulonate monohydrate in a lower alcohol with acid at a pH in a range from about 1.5 to about 3.5 whereby the acid is converted to the insoluble sodium salt of the acid and the sodium 2-keto-L-gulonate monohydrate is converted to free 2-keto-L-gulonic acid; and d) removing the sodium salt of the acid to obtain an alcoholic solution of 2-keto-L-gulonic acid.

2. The process of claim 1, further comprising mechanically reducing the crystal size of the sodium 2-keto-L-gulonate monohydrate crystals recovered in step b prior to their suspension in the alcohol.

3. The process of claim 1, wherein step c comprises firstly suspending the sodium 2-keto-L-gulonate monohydrate crystals in the alcohol, leaving the crystals to swell and subsequently adding an acid to adjust the pH to from about 1.5 to about 3.5.

4. The process of claim 1, wherein step c comprises suspending the sodium 2-keto-L-gulonate monohydrate crystals in the alcohol while simultaneously adding an acid to adjust the pH to from about 1.5 to about 3.5.

5. The process of claim 1, wherein step c comprises firstly suspending the sodium 2-keto-L-gulonate monohydrate crystals in the alcohol, leaving the crystals to swell and subsequently performing a wet grinding of the crystals while adding acid to adjust the pH to from about 1.5 to about 3.5.

6. The process of claim 3 wherein the lower alcohol of step b is selected from the group consisting of methanol, propanol and glycol.

7. The process of claim 4 wherein the lower alcohol of step b is selected from the group consisting of methanol, ethanol, propanol and glycol.

8. The process of claim 5 wherein the lower alcohol of step b is selected from the group consisting of methanol, ethanol, propanol and glycol.

9. The process of claim 1 wherein the crystallization of step a is accomplished by continuous evaporation crystallization.

10. The process of claim 3 wherein the acid added to the in step c is selected from the group consisting of concentrated sulphuric acid, phosphoric acid, hydrochloric acid, nitric acid and gaseous hydrogen chloride.

11. The process of claim 4 wherein the acid added in step c is selected from the group consisting of concentrated sulphuric acid, phosphoric acid, hydrochloric acid, nitric acid and gaseous hydrogen chloride.

12. The process of claim 5 wherein the acid added in step c is selected from the group consisting of concentrated sulphuric acid, phosphoric acid, hydrochloric acid, nitric acid and gaseous hydrogen chloride.

13. The process of claim 3 wherein the pH is adjusted from about 2.5 to about 3.5.

14. The process of claim 4 wherein the pH is adjusted from about 2.5 to about 3.5.

15. The process of claim 5 wherein the pH is adjusted from about 2.5 to about 3.5.

16. The process of claim 1 wherein the step c is carried out at a temperature between about 20° C. and about 70° C.

17. The process of claim 1 wherein the removal of the salt of the acid formed is carried out by centrifugation.

18. The process of claim 1, wherein the crystallization of the sodium 2-keto-L-gulonate monohydrate of step a is accomplished by evaporation crystallization, the separation of the sodium 2-keto-L-gulonate monohydrate crystals is accomplished by centrifugation, the alcohol in which the sodium 2-keto-L-gulonate monohydrate crystals are suspended in step c is methanol, the acid used to acidify the suspension in step c is sulphuric acid with a concentration of greater than 95% and the removal of the salt of the acid formed is carried out by centrifugation.

* * * * *